(12) United States Patent
Chackerian et al.

(10) Patent No.: US 12,121,574 B2
(45) Date of Patent: Oct. 22, 2024

(54) MALARIA IMMUNOGEN AND METHODS FOR USING SAME

(71) Applicants: UNM RAINFOREST INNOVATIONS, Albuquerque, NM (US); THE JOHNS HOPKINS UNIVERSITY, Baltimore, MD (US); VAXINE PTY LTD., Bedford Park (AU)

(72) Inventors: Bryce C. Chackerian, Albuquerque, NM (US); Fidel P. Zavala, Baltimore, MD (US); David S. Peabody, Albuquerque, NM (US); Nikolai Petrovsky, Adelaide (AU); Lucie Jelinkova, Albuquerque, NM (US)

(73) Assignees: UNM RAINFOREST INNOVATIONS, Albuquerque, NM (US); THE JOHNS HOPKINS UNIVERSITY, Baltimore, MA (US); VAXINE PTY LTD., Bedford Park (AU)

( * ) Notice: Subject to any disclaimer, the term of this patent is extended or adjusted under 35 U.S.C. 154(b) by 0 days.

(21) Appl. No.: 17/953,712

(22) Filed: Sep. 27, 2022

(65) Prior Publication Data

US 2023/0102159 A1    Mar. 30, 2023

Related U.S. Application Data

(60) Provisional application No. 63/249,281, filed on Sep. 28, 2021.

(51) Int. Cl.
*A61K 39/002* (2006.01)
*A61K 39/00* (2006.01)
*A61K 39/015* (2006.01)
*A61P 33/06* (2006.01)
*C12N 15/63* (2006.01)

(52) U.S. Cl.
CPC ............ *A61K 39/015* (2013.01); *A61P 33/06* (2018.01); *C12N 15/63* (2013.01); *A61K 2039/5258* (2013.01); *A61K 2039/55561* (2013.01)

(58) Field of Classification Search
None
See application file for complete search history.

(56) References Cited

U.S. PATENT DOCUMENTS

| | | | |
|---|---|---|---|
| 4,722,840 | A | 2/1988 | Valenzuela et al. |
| 5,234,809 | A | 8/1993 | Boom et al. |
| 7,776,616 | B2 | 8/2010 | Heath et al. |
| 7,957,913 | B2 | 6/2011 | Chinitz et al. |
| 9,012,208 | B2 | 4/2015 | Selden et al. |

FOREIGN PATENT DOCUMENTS

| | | | |
|---|---|---|---|
| EP | 0421635 | B1 | 7/1995 |
| WO | 0032227 | A2 | 6/2000 |
| WO | 02056905 | A2 | 7/2002 |
| WO | WO 2003/024481 | * | 3/2003 |
| WO | 03092714 | A2 | 11/2003 |
| WO | 2004007538 | A2 | 1/2004 |
| WO | WO 2018/148660 | * | 8/2018 |
| WO | 2018193063 | A2 | 10/2018 |
| WO | 2021016509 | A1 | 1/2021 |

OTHER PUBLICATIONS

Anker et al., "$V_H$ and $V_L$ region structure of antibodies that recognize the (NANP)$_3$ dodecapeptide sequence in the circumsporozoite protein of *Plasmodium falciparum*," Dec. 1990, European Journal of Immunology, 20(12):2757-2761.

Espinosa et al., "Development and Assessment of Transgenic Rodent Parasites for the Preclinical Evaluation of Malaria Vaccines," 2016, Methods in Molecular Biology, 1403:583-601.

Green et al., *Molecular Cloning: A Laboratory Manual*, Fourth Edition, Cold Spring Harbor Laboratory Press, Woodbury, NY, 2012, Cover page, title page and table of contents.

Aida et al., "Removal of endotoxin from protein solutions by phase separation using Triton X-114," Journal of immunological Methods, Sep. 14, 1990, vol. 132, No. 2, pp. 191-195.

Atcheson et al., "A VLP for validation of the Plasmodium falciparum circumsporozoite protein junctional epitope for vaccine development," npj Vaccines, Apr. 1, 2021, vol. 6, No. 46, pp. 1-9.

Calvo-Calle et al., "Identification of a neutralizing epitope within minor repeat region of Plasmodium falciparum CS protein," npj Vaccines, Jan. 18, 2021, vol. 6, No. 10, pp. 1-8.

Fialova et al., "Comparison of different enzyme-linked immunosorbent assay methods for avidity determination of antiphospholipid antibodies," Journal of Clinical Laboratory Analysis, Nov. 2017, vol. 31, No. 6, pp. 1-9.

Flores-Garcia et al., "Optimization of an in vivo model to study immunity to Plasmodium falciparum pre-erythrocytic stages," Malaria Journal, Dec. 2019, vol. 18, pp. 1-9.

(Continued)

*Primary Examiner* — Jennifer E Graser
(74) *Attorney, Agent, or Firm* — MUETING RAASCH GROUP

(57) ABSTRACT

An immunogen useful for treating malaria generally includes an immunogenic carrier and an antigenic malaria circumsporozoite protein (CSP) peptide that includes the peptide NANPNVDPNANPNVD (SEQ ID NO:2) linked to the immunogenic carrier. The immunogen may be administered to a subject having or at risk of having malaria. Alternatively, the immunogen may be administered to an individual having or at risk of having *Plasmodium falciparum* blood stage parasitemia. In some cases, the immunogen can be administered in combination with another therapeutic agent for treating malaria of *Plasmodium falciparum* blood stage parasitemia.

32 Claims, 4 Drawing Sheets
Specification includes a Sequence Listing.

(56) References Cited

OTHER PUBLICATIONS

Francica et al., "Design of alphavirus virus-like particles presenting circumsporozoite junctional epitopes that elicit protection against malaria," Vaccines, Mar. 18, 2021, vol. 9, No. 272, pp. 1-15.
International Preliminary Report on Patentability for PCT/US2020/043375, issued Jan. 25, 2022, 8 pages.
International Search Report and Written Opinion for PCT/US2020/043375, issued Oct. 8, 2020, 11 pages.
Jelinkova et al., "A vaccine targeting the L9 epitope of the malaria circumsporozoite protein confers protection from blood-stage infection in a mouse challenge model," npj Vaccines, 2022, vol. 34, pp. 1-4.
Jelinkova et al., "An epitope-based malaria vaccine targeting the junctional region of circumsporozoite protein," npj Vaccines, 2021, vol. 6, No. 13, pp. 1-10.
Kisalu et al., "A human monoclonal antibody prevents malaria infection and defines a new site of vulnerability on Plasmodium falciparum circumsporozoite protein," Nature Medicine, May 2018, vol. 24, pp. 408-416.
Kozlovska et al., "RNA phage Qβ coat protein as a carrier for foreign epitopes," Intervirology, 1996, vol. 39, No. 1-2, pp. 9-15.
Noe et al., "A full-length Plasmodium falciparum recombinant circumsporozoite protein expressed by Pseudomonas fluorescens platform as a malaria vaccine candidate," PloS One, Sep. 23, 2014, vol. 9, No. 9, pp. 1-15.
Olotu et al., "Seven-year efficacy of RTS, S/AS01 malaria vaccine among young African children," New England Journal of Medicine, Jun. 30, 2016, vol. 374, No. 26, pp. 2519-2529.
Oyen et al., "Structure and mechanism of monoclonal antibody binding to the junctional epitope of Plasmodium falciparum circumsporozoite protein," PLoS Pathogens, Mar. 9, 2020, vol. 16, No. 3, pp. 1-22.
Penny et al., "The time-course of protection of the RTS, S vaccine against malaria infections and clinical disease," Malaria Journal, 2015, vol. 14, No. 437, pp. 1-13.
Petrovsky et al., "Advax™, a novel microcrystalline polysaccharide particle engineered from delta inulin, provides robust adjuvant potency together with tolerability and safety," Vaccine, Nov. 4, 2015, vol. 33, No. 44, pp. 5920-5926.
RTS, S Clinical Trials Partnership, "Efficacy and safety of RTS, S/AS01 malaria vaccine with or without a booster dose in infants and children in Africa: final results of a phase 3, individually randomised, controlled trial," Lancet, Jul. 4, 2015, vol. 386, No. 9988, pp. 31-45.
Schneider et al., "NIH Image to ImageJ: 25 years of image analysis," Nature Methods, Jul. 2012, vol. 9, No. 7, pp. 671-675.
Smiley et al., "Enhanced readthrough of opal (UGA) stop codons and production of Mycoplasma pneumoniae P1 epitopes in *Escherichia coli*," Gene, Nov. 30, 1993, vol. 134, No. 1, pp. 33-40.
Stoute et al., "A preliminary evaluation of a recombinant circumsporozoite protein vaccine against Plasmodium falciparum malaria," New England Journal of Medicine, Jan. 9, 1997, vol. 336, No. 2, pp. 86-91.
Tan et al., "A public antibody lineage that potently inhibits malaria infection through dual binding to the circumsporozoite protein," Nature Medicine, May 2018, vol. 24, No. 4, pp. 401-407.
Tatusova et al., "BLAST 2 Sequences, a new tool for comparing protein and nucleotide sequences," FEMS Microbiology Letters, May 1, 1999, vol. 174, No. 2, pp. 247-250.
Tumban et al., "A pan-HPV vaccine based on bacteriophage PP7 VLPs displaying broadly cross-neutralizing epitopes from the HPV minor capsid protein, L2," PloS One, Aug. 17, 2011, vol. 6, No. 8, pp. 1-11.
Wang et al., "A potent anti-malarial human monoclonal antibody targets circumsporozoite protein minor repeats and neutralizes sporozoites in the liver," Immunity, Oct. 13, 2020, vol. 53, No. 4, pp. 733-744.

\* cited by examiner

MALARIA IMMUNOGEN AND METHODS FOR USING SAME

CROSS-REFERENCE TO RELATED APPLICATION

This application claims the benefit of U.S. Provisional Patent Application No. 63/249,281, filed Sep. 28, 2021, which is incorporated herein by reference in its entirety.

GOVERNMENT FUNDING

This invention was made with government support under AI061142 and AI007538 awarded by the National Institutes of Health. The government has certain rights in the invention.

SEQUENCE LISTING

This application contains a Sequence Listing electronically submitted to the United States Patent and Trademark Office via EFS-Web as an ASCII text file entitled "0310-000170US01.txt" having a size of 2040 bytes and created on Sep. 27, 2022. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

SUMMARY

This disclosure describes, in one aspect, an immunogen useful for treating malaria. Generally, the immunogen includes an immunogenic carrier and an antigenic malaria circumsporozoite protein (CSP) peptide that includes NANPNVDPNANPNVD (SEQ ID NO:2) linked to the immunogenic carrier.

In one or more embodiments, the immunogenic carrier is linked to the CSP peptide through a succinimidyl-6-[β-maleimidopropionamido]hexanoate (SMPH) cross-linker molecule.

In one or more embodiments, the immunogen includes second antigenic malaria circumsporozoite protein (CSP) peptide. In one or more of these embodiments, SEQ ID NO:2 and the second antigenic CSP peptide are displayed on a single VLP.

In another aspect, this disclosure describes a composition that includes an immunogen that includes an immunogenic carrier and an antigenic malaria circumsporozoite protein (CSP) peptide that includes NANPNVDPNANPNVD (SEQ ID NO:2) linked to the immunogenic carrier.

In one or more embodiments, the composition includes VLPs that display SEQ ID NO:2 and a second antigenic CSP peptide.

In one or more embodiments, the composition includes a first population of VLPSEQ ID NO:2 and a second population of VLPs displaying the second antigenic CSP peptide.

In one or more embodiments, the composition further includes an adjuvant.

In another aspect, this disclosure describes a method of treating malaria in an individual. Generally, the method includes administering a therapeutically effective amount of a composition to the individual, the composition including an immunogenic carrier and an antigenic malaria circumsporozoite protein (CSP) peptide comprising NANPNVDPNANPNVD (SEQ ID NO:2) linked to the immunogenic carrier.

In one or more embodiments, the method further includes administering to the individual at least one additional therapeutic agent for treating malaria.

In one or more embodiments, the composition further comprises a second antigenic malaria circumsporozoite protein (CSP) peptide displayed on an immunogenic carrier. In one or more of these embodiments, SEQ ID NO:2 and the second antigenic CSP peptide are linked to a single immunogenic carrier.

In one or more embodiments, the composition includes a first population of immunogens and a second population of immunogens. Generally, the first immunogen includes immunogenic carriers and CSP peptides that include SEQ ID NO:2 linked to the immunogenic carriers. Generally, the second population of immunogens includes immunogenic carriers and a second CSP peptide linked to the immunogenic carriers.

In one or more embodiments, the composition is administered to the individual before the individual manifests a symptom or clinical sign of malaria.

In another aspect, this disclosure describes a nucleic acid encoding any embodiments of an immunogen that includes an immunogenic carrier and an antigenic malaria circumsporozoite protein (CSP) peptide that includes NANPNVDPNANPNVD (SEQ ID NO:2) linked to the immunogenic carrier.

In another aspect, this disclosure describes an expression vector that includes a nucleic acid encoding any embodiments of an immunogen that includes an immunogenic carrier and an antigenic malaria circumsporozoite protein (CSP) peptide that includes NANPNVDPNANPNVD (SEQ ID NO:2) linked to the immunogenic carrier.

In another aspect, this disclosure describes a host cell that includes an expression vector that includes a nucleic acid encoding any embodiments of an immunogen that includes an immunogenic carrier and an antigenic malaria circumsporozoite protein (CSP) peptide that includes NANPNVDPNANPNVD (SEQ ID NO:2) linked to the immunogenic carrier.

In another aspect, this disclosure describes a vaccine that includes an immunogen that includes an immunogenic carrier and an antigenic malaria circumsporozoite protein (CSP) peptide that includes NANPNVDPNANPNVD (SEQ ID NO:2) linked to the immunogenic carrier.

In another aspect, this disclosure describes a method of treating malaria in an individual. Generally, the method includes administering to the individual a therapeutically effective amount of a vaccine that includes an immunogen that includes an immunogenic carrier and an antigenic malaria circumsporozoite protein (CSP) peptide that includes NANPNVDPNANPNVD (SEQ ID NO:2) linked to the immunogenic carrier.

In one or more embodiments, the method further includes administering to the individual at least one additional therapeutic agent for treating malaria.

In one or more embodiments, the vaccine further includes a second antigenic malaria circumsporozoite protein (CSP) peptide. In one or more of these embodiments, SEQ ID NO:2 and the second antigenic CSP peptide are linked to a single carrier.

In one or more embodiments, the vaccine includes a first population of immunogens and a second population of immunogens. Generally, the first population of immunogens includes immunogenic carriers and CSP peptides that include SEQ ID NO:2 linked to the immunogenic carriers. Generally, the second population of immunogens includes immunogenic carriers and a second CSP peptide linked to the immunogenic carriers.

In one or more embodiments, the vaccine is administered to the individual before the individual manifests a symptom or clinical sign of malaria.

In another aspect, this disclosure describes method of treating *Plasmodium falciparum* blood stage parasitemia in an individual. Generally, the method includes administering to the individual a therapeutically effective amount of a vaccine that includes an immunogen that includes an immunogenic carrier and an antigenic malaria circumsporozoite protein (CSP) peptide that includes NANPNVDPNANPNVD (SEQ ID NO:2) linked to the immunogenic carrier.

In one or more embodiments, the vaccine further includes a second antigenic malaria circumsporozoite protein (CSP) peptide. In one or more of these embodiments, SEQ ID NO:2 and the second antigenic CSP peptide are linked to a single carrier.

In one or more embodiments, the vaccine includes a first population of immunogens and a second population of immunogens. Generally, the first population of immunogens includes immunogenic carriers and CSP peptides that include SEQ ID NO:2 linked to the immunogenic carriers. Generally, the second population of immunogens includes immunogenic carriers and a second CSP peptide linked to the immunogenic carriers.

In one or more embodiments, the vaccine is administered to the individual before the individual manifests a symptom or clinical sign of *Plasmodium falciparum* blood stage parasitemia.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
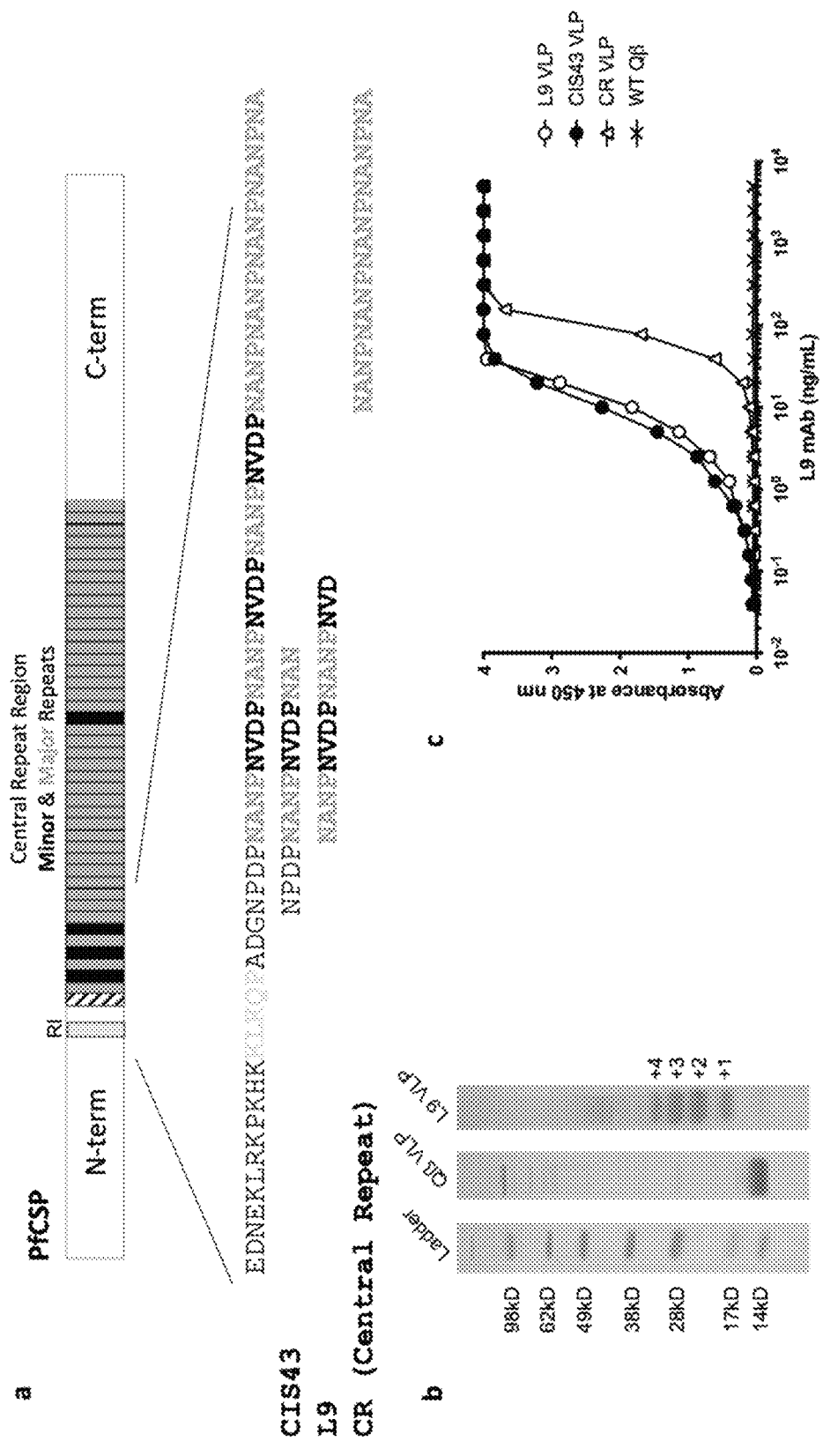
FIG. 1. Characterization data for the L9 VLPs. (A) Structure of PfCSP and the amino acid sequences (SEQ ID NO:1) targeted in this study. CSP contains an N-terminal region, which contains the RI cleavage site (RI), a Junction region (between RI and the central repeat), and the Central Repeat Region, which contains four NVDP minor repeats and more than 35 NANP major repeats. The primary amino acid targets of mAbs CIS43 (amino acids 21-35 of SEQ ID NO:1) and L9 (SEQ ID NO: 2; amino acids 25-39 of SEQ ID NO:1) are shown along with the sequence of a Central Repeat (CR) (amino acids 49-66 of SEQ ID NO:1) peptide representing the major repeats. (B) SDS-PAGE analysis of unconjugated (center lane) or L9 peptide conjugated (right lane) Qβ VLPs. The ladder of bands in the L9 VLP lane reflect individual copies of coat protein modified with one, two, three, or more copies of the L9 peptide. Gel images are derived from the same experiment and were processed in parallel. Size markers are shown in the left lane. The unmodified gel is shown in FIG. 3. (C) Binding of the L9 mAb to L9 VLPs (o), CIS43 VLPs (•), VLPs displaying the CR peptide (Δ), or wild-type (unmodified) Qβ VLPs (X) as measured by ELISA.

This disclosure describes antigenic malaria circumsporozoite protein (CSP) peptides useful in making a vaccine against malaria, methods of preparing a vaccine that includes an antigenic CSP peptide, and methods of treatment that includes administering an antigenic CSP peptide vaccine to a subject.

Malaria is a significant global public health concern. A disproportionate share of malarial disease and deaths occurs in Africa and is caused by infection with the *Plasmodium falciparum* parasite. *P. falciparum* (Pf) infection is initiated when the *Anopheles* mosquito injects sporozoites into the blood stream of a human host. Sporozoites are transported quickly to the liver where they transiently multiply within hepatocytes, producing merozoites, which then enter the blood stream where they invade red blood cells (RBCs), replicate further, and cause the symptoms and pathology of malaria.

A number of different malaria vaccine strategies have been proposed, including vaccines that target transmission, the erythrocytic stage in which symptoms occur, and the pre-erythrocytic stage. A pre-erythrocytic vaccine that effectively blocks malaria infection of hepatocytes could potentially provide sterilizing immunity against malaria. However, development of such a vaccine has been complicated by a number of factors, including (1) natural immunity to the pre-erythrocytic stage is weak and ineffective, (2) surface antigens expressed on sporozoites are antigenically variable, and (3) high titers of circulating antibody are likely required to effectively inhibit infection.

Most attempts to develop pre-erythrocytic vaccines have targeted the malaria circumsporozoite protein (CSP). CSP is the most abundant protein on the surface of the malaria sporozoite and is an attractive vaccine target because anti- CSP antibodies reduce the likelihood and/or extent that the malaria parasite reaches the liver and establishes infection. Malarial vaccines targeting the central repeat (CR) region of the CSP (FIG. 1A, amino acids 49-66 of SEQ ID NO:1) only moderately reduce human infection. For example, CSP is the target of RTS,S/AS01 (also referred to as RTS,S), the most advanced malaria vaccine. However, the RTS,S vaccine confers only moderate (30-50%) reduction of clinical infection and immunity rapidly declines. Thus, there remains a need for a malaria vaccine with higher potency and provides more durable immune responses than the RTS,S vaccine.

Human monoclonal antibodies (mAbs) from human volunteers immunized with an experimental irradiated whole sporozoite vaccine (PfSPZ) that target amino acid residues in the CSP but outside of the central repeat region have shown the ability to reduce malaria infection in animal models, which points to new sites of vulnerability in CSP that may be exploited using epitope-targeted vaccines.

Most previous CSP-targeted vaccines have used full-length or near full-length antigen. RTS,S, for example, contains a large domain of the CSP central-repeat region and most of its C-terminal domain. While a subset of antibodies elicited by RTS,S reduce infection, using large domains of an antigen can be problematic as critical epitopes may be hidden or immunologically subdominant.

International Patent Application No. PCT/2020/043375 (International Publication No. WO 2021/016509 A1) discloses a bacteriophage Qβ-based virus-like particle (VLP) vaccine that multivalently displays a peptide recognized by the CIS43 mAb, which is located at the junction between the N-terminal region of CSP and the CR (FIG. 1A), can elicit extremely durable and high-titer anti-CSP antibody responses, and reduce parasite liver burden in a mouse malaria challenge model, but did not prevent blood-stage parasitemia.

This disclosure describes the development and characterization of a bacteriophage VLP-based vaccine targeting the amino acid residues recognized by the L9 mAb, a newly described anti-CSP antibody (Wang et al. *Immunity* 53, 733-744 e738 (2020)). The amino acids recognized by the L9 mAb (SEQ ID NO:2) overlap with the amino acid recognized by the CIS43 mAb (amino acids 21-35 of SEQ ID NO:1), but is centered on the minor repeat sequences at the N-terminus of the central repeat region (FIG. 1A). Despite their similarity in sequence, the L9-based vaccine described herein was able to reduce parasite liver load (FIG. 2C) and reduce blood stage parasitemia (FIG. 2D) in a malaria challenge experiment with a higher efficacy than a comparable CIS43-based vaccine.

VLP Display

Many viral structural proteins have an intrinsic ability to self-assemble into virus-like particles (VLPs), which structurally resemble the virus from which they were derived but, because they lack viral genomes, they are absolutely non-infectious. VLPs not only can serve as stand-alone vaccines, but because their particulate nature and multivalent structure provoke strong immune responses, they can be used as platforms to enhance the immunogenicity of heterologous antigenic targets. For example, when short immunogenic peptides are displayed in a highly repetitive, multivalent fashion on VLPs, peptide-specific B cells are strongly activated, leading to high-titer, long-lasting antibody responses. VLPs derived from diverse virus types can serve as effective platforms for antigen display. The immunogens described herein are based on VLPs derived from a family of related single-stranded RNA bacteriophages, including MS2, PP7, AP205, and Qβ. These VLPs can be produced by expressing a single viral structural protein, called coat, from a plasmid in a bacterium. Peptides may be displayed on a VLP by bioconjugation techniques using cross linker molecules. In one or more embodiments, a peptide may be displayed on a VLP by conjugating the peptide to the VLP through a succinimidyl maleimidopropionamido]hexanoate (SMPH) cross-linker molecule. This technique results in VLPs that display target peptides at high valency, usually 180-360 peptides per VLP, and confers strong immunogenicity to displayed immunogenic peptides.

ADVAX Adjuvant Platform

While alum remains the dominant adjuvant used in human vaccines worldwide, it has shown poor utility in malaria vaccines, with oil emulsions and more complex adjuvant combinations such as AS01 delivering more favorable results in human studies. However, oil emulsion adjuvants are associated with high reactogenicity and the ability of the RTS,S/AS01 vaccine to reduce infection attenuates rapidly. A major malaria vaccine challenge is to find a suitable adjuvant platform that overcomes these obstacles. This adjuvant platform needs to be able to drive strong and long-lasting humoral and cellular immune responses while being non-reactogenic and safe for use in young children. ADVAX (Vaxine Pty, Ltd., Adelaide, Australia) was developed as a polysaccharide particle adjuvant platform based on the plant sugar, delta inulin (Petrovsky et al., 2015, Vaccine 33:5920-5926) to further enhance its adjuvant potency, ADVAX can be co-formulated with a toll-like receptor (TLR) agonists such as a CpG oligonucleotide (e.g., CpG55.2) that activates TLR9 and/or an imidazoquinoline amine that activates TLR7 and/or TLR8. This results in highly effective vaccine formulations that can induce immunity after just one immunization sufficient to inhibit infection, generate longer lasting and more broadly cross-neutralizing antibodies, and production of durable memory CD4 and CD8 T cell responses (Petrovsky et al., 2015, Vaccine 33:5920-5926). These adjuvant formulations can be designed to shape the immune response in any desired direction, e.g. Th1, Th2, or Th17, that correlates best with immunity. Further, these adjuvants can be formulated with one or more additional ingredients such as, for example, aluminum hydroxide.

Construction and Antigenicity of L9 VLPs

Qβ VLPs that multivalently display the 15-amino-acid sequence (SEQ ID NO: 2) recognized by the L9 mAb (L9 VLPs) by chemically conjugating a synthetic L9 peptide to the surface of VLP using a bifunctional crosslinker where constructed. While described below in the context of an exemplary embodiment in which the VLP platform used to present the antigenic CSP peptide is a Qβ VLP, the compositions and methods described herein can involve the use of any suitable VLP platform. Thus, as noted above, VLPs that present an antigenic CSP peptide can be derived from any one of a family of related single-stranded RNA bacteriophages including, but not limited to, MS2, PP7, AP205, or Qβ.

L9 VLPs display an average of 385 copies of the immunogenic peptide per VLP (FIG. 1B) and are strongly bound by the L9 mAb (FIG. 1C). L9 mAb also binds strongly to CIS43 VLPs, but less strongly to VLPs displaying a peptide representing the major repeat sequence (CR VLP). L9 VLPs are highly immunogenic in mice; three doses of unadjuvanted L9 VLPs elicited high titer and durable anti-CSP antibodies (FIG. 2A), as was previously observed in mice immunized with CIS43 VLPs (Jelinkova et al. *NPJ Vaccines* 6, 13 (2021)). L9 VLPs elicit antibodies that inhibit binding of the L9 mAb to CSP (FIG. 3), suggesting that they have a similar specificity as the L9 mAb.

Figure 2:
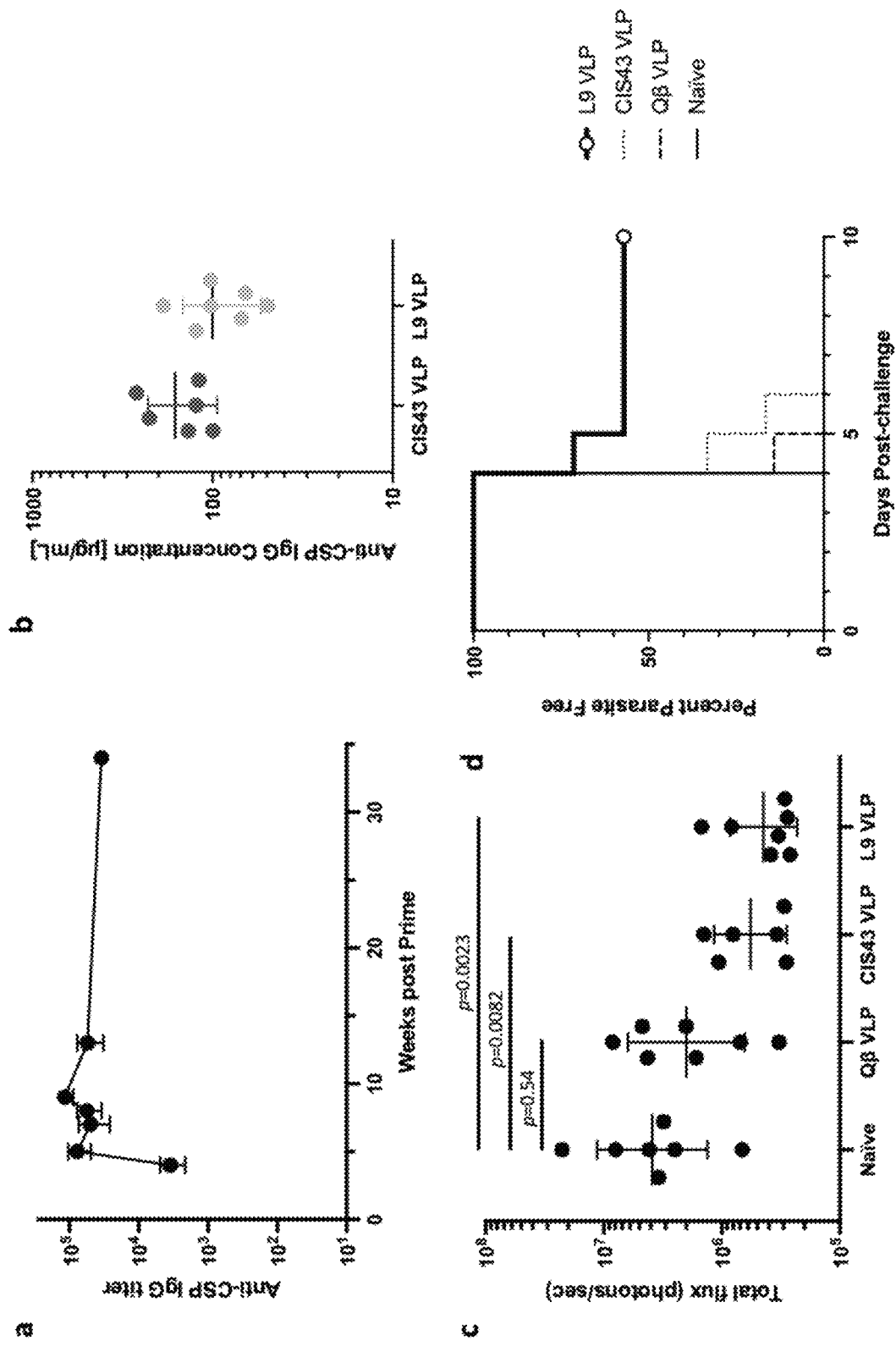
FIG. 2. L9 VLPs elicit strong and long-lasting anti-CSP antibody responses that reduce parasitemia. (A) Mean anti-CSP IgG concentrations sampled over 34 weeks in Balb/c mice (n=6/group) immunized three times (at week zero, week four, and week seven) with L9 VLPs without adjuvant. Error bars represent SEM. (B) Anti-CSP antibody concentrations in C57BL6 mice immunized three times with CIS43 VLPs or L9 VLPs, both with ADVAX-3 adjuvant (n=6-7/group). (C) Parasite liver load (as measured by luminescence) in CIS43 VLP and L9 VLP-vaccinated (or control) C57BL6 mice (n=6-7/group) following mosquito challenge. The Mann-Whitney test was used to statistically compare each group to the naive group. (D) Percent of parasite free mice post-challenge as evaluated by Giemsa blood smear.
Figure 3:
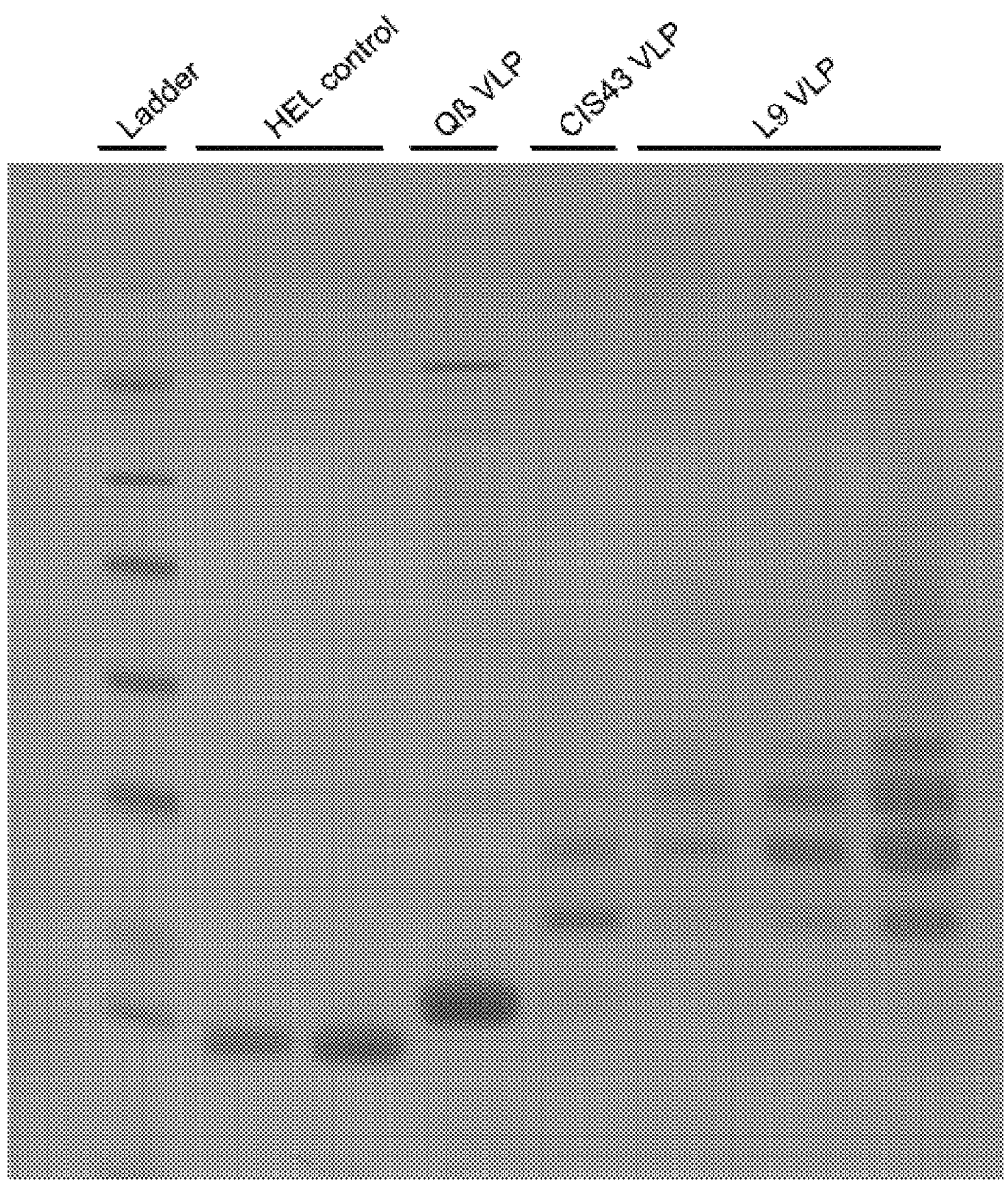
FIG. 3 shows the unmodified gel used as the source of data shown in FIG. 1B. Lane one (left) contains molecular weight markers (Invitrogen, Waltham, MA; SEEBLUE PLUS2 Prestained Markers). Lanes two and three contain different amounts of Hen Egg Lysozyme (Gold Biotechnology, St. Louis, MO). Lane four contains unconjugated Qβ VLPs. Lane five contains CIS43 peptide conjugated VLPs. Lanes six-eight contain different amounts of L9 peptide conjugated VLPs. Lanes one, four, and eight are shown in FIG. 1B.
Figure 4:
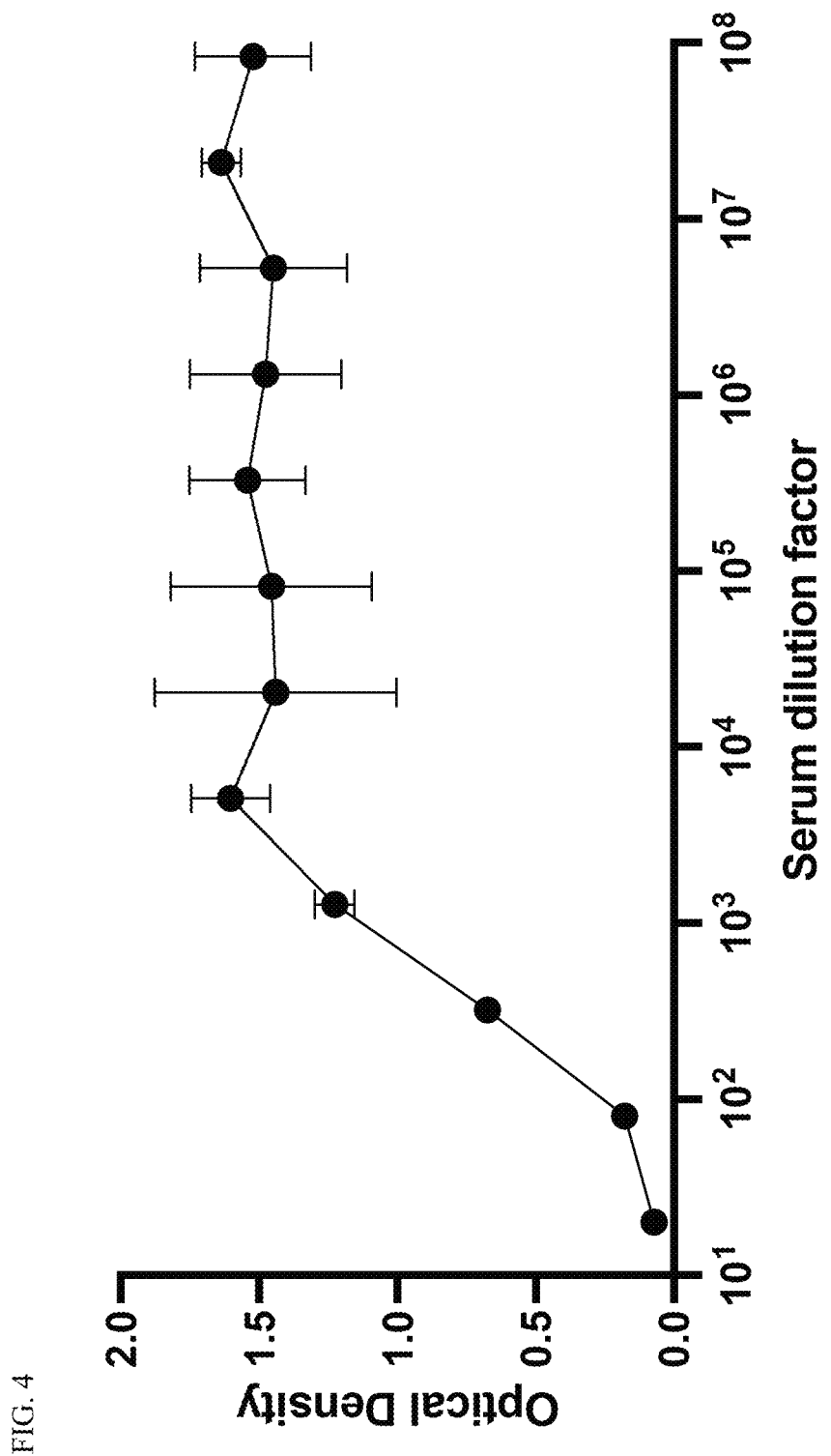
FIG. 4 shows data indicating that L9 VLP immunized mouse sera block the binding of mAb L9 to CSP. Pooled sera from L9 VLP-immunized mice (n=six) were tested for inhibition of L9 mAb to CSP by competition ELISA. This experiment was performed in duplicate and error bars represent SEM.

To test whether L9 VLPs could reduce infection from malaria challenge, C57Bl/6 mice were vaccinated with L9 VLPs, CIS43 VLPs, or, as a negative control, wild-type Qβ VLPs and then challenged with malaria-infected mosquitoes. International Patent Application No. PCT/2020/043375 (International Publication No. WO 2021/016509 A1) has disclosed that co-administration of CIS43 VLPs with the adjuvant ADVAX-3, which is a mixture of CpG55.2 oligonucleotide (a TLR9 agonist) with aluminum hydroxide, could increase anti-CSP antibody levels. Therefore, all vaccines described herein were adjuvanted with ADVAX-3. As is shown in FIG. 2B, both L9 VLPs and CIS43 VLPs mixed with ADVAX-3 elicited strong anti-CSP antibody responses. After three immunizations, mice were exposed to mosquitoes infected with luciferase-reporter containing transgenic *P. berghei* (Pb) engineered to express full-length PfCSP in place of PbCSP (Pb-PfCSP-Luc). Forty-two hours after challenge, liver parasite loads were measured using an intravital imaging system. Mice immunized with CIS43 VLPs and L9 VLPs had significantly lower liver parasite loads than control VLP-vaccinated mice or unvaccinated (naïve) controls (FIG. 2C). Relative to naïve mice, immunization with CIS43 VLPs reduced mean parasite loads by ~89% (similar to what has been show previously (Jelinkova et al. *NPJ Vaccines* 6, 13 (2021); International Publication No. WO 2021/016509 A1) and immunization with L9 VLPs reduced mean parasite loads by ~92%. Beginning four days after infection, blood smears from mice were evaluated for parasitemia. While all control mice and CIS43 VLP-immunized mice developed blood stage parasitemia, four of the seven mice immunized with L9 VLPs remained parasite-free ten days after infection, indicating that the vaccine inhibited infection from the parasite challenge (FIG. 2D).

The efficacy of vaccines targeting two overlapping immunogenic peptides within the junctional/minor repeat regions of *Plasmodium falciparum* CSP that are recognized by the potent inhibitory monoclonal antibodies, CIS43 and L9, is evaluated and compared. VLPs displaying both immunogenic peptides could elicit strong anti-CSP antibody responses and could significantly reduce parasite liver loads in experimentally challenged mice. However, only L9 VLPs reduced the likelihood and extent of blood parasitemia, indicating functional sterilizing immunity. The 15-amino-acid CIS43 and L9 immunogenic peptides overlap by 11 amino acids, suggesting that subtle changes in the immunogenic peptide targeted by an anti-CSP antibody can dramatically affect the ability of the vaccine to inhibit infection. The most potent anti-CSP mAbs may recognize immunogenic peptides derived from the joining of minor and major tetrapeptide repeats, including DPNA (major/minor) and NPNV (minor/major). The DPNA motif is found twice in the CIS43 immunogenic peptide and once in the L9 immunogenic peptide, whereas NPNV is found twice in the L9 immunogenic peptide and once in the CIS43 immunogenic peptide. Thus, antibodies that target NPNV may be more functionally active. Taken together, these studies indicate that L9 VLPs are a promising malaria vaccine candidate.

Thus, this disclosure describes a VLP-based immunogen that specifically targets CSP. These particles are highly immunogenic in both mouse and macaque models and elicit a long-lived antibody response. To increase the immunogenicity of L9 VLPs, the L9 VLPs can be combined with an adjuvant. Suitable adjuvants include, but are not limited to, delta inulin polysaccharide-based ADVAX adjuvants. In particular, combining L9 VLPs with ADVAX-3 or ADVAX-4 yields higher anti-CSP antibody titers than unadjuvanted L9 VLPs.

The VLP-based immunogen includes an antigenic CSP peptide (also referred to herein as a "a CSP-targeting peptide") such as, for example, the amino acids of SEQ ID NO:2 (amino acids 25-39 of SEQ ID NO:1 or a structurally similar peptide. Further, the immunogen can include a VLP that displays more than one population of antigenic CSP peptides—e.g., a first population of antigenic CSP peptides that includes the amino acids of SEQ ID NO:2 (or a structurally similar peptide) and a second population of antigenic CSP peptides that includes amino acids 21-35 of SEQ ID NO:1, amino acids 49-66 of SEQ ID NO:1, any other immunogenic CSP peptide described in the International Patent Application No. PCT/2020/043375 (International Publication No. WO 2021/016509 A1), or a peptide structurally similar to any of the foregoing. Thus, the immunogen can be designed to display one, two, three, four, five, six, or more antigenic CSP peptides.

In another aspect, an immunogenic composition may include more than one population of VLPs. For example, an immunogenic composition can include a first population of VLPs displaying the antigenic CSP peptide including the amino acids SEQ ID NO:2 (or a structurally similar peptide) and a second population of VLPs displaying a second antigenic CSP peptide. Exemplary second antigenic CSP peptides include, but are not limited to, amino acids 21-35 of SEQ ID NO:1, amino acids 49-66 of SEQ ID NO:1, any other immunogenic CSP peptide described in the International Patent Application No. PCT/2020/043375 (International Publication No. WO 2021/016509 A1), or a peptide structurally similar to any of the foregoing. As another example, an immunogenic composition may include a first population of VLPs displaying one or more antigenic CSP peptides and a second population of VLPs displaying one or more antigenic CSP peptides, independent of the number and identity of the antigenic peptides displayed by the first population of VLPs.

As used herein, a peptide is "structurally similar" to a reference polypeptide if the amino acid sequence of the peptide possesses a specified amount of identity compared to the reference peptide. Structural similarity of two peptides can be determined by aligning the residues of the two peptides (for example, a candidate polypeptide and SEQ ID NO:2) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate peptide is the peptide being compared to the reference peptide (e.g., SEQ ID NO:2). A candidate peptide can be isolated, for example, from an animal, or can be produced using recombinant techniques, or chemically or enzymatically synthesized.

A pair-wise comparison analysis of amino acid sequences can be carried out using the BESTFIT algorithm in the GCG package (version 10.2, Madison WI). Alternatively, peptides may be compared using the Blastp program of the BLAST 2 search algorithm, as described by Tatiana et al., (*FEMS Microbiol Lett*, 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

An antigenic CSP peptide can include amino acids in addition to SEQ ID NO:1, so long as the additional amino acids do not eliminate immunogenicity toward CSP. For example, an antigenic CSP peptide may have a linker region containing the amino acids GGGC (SEQ ID NO: 3).

In the comparison of two amino acid sequences, structural similarity may be referred to by percent "identity" or may be referred to by percent "similarity." "Identity" refers to the presence of identical amino acids. "Similarity" refers to the presence of not only identical amino acids but also includes the presence of conservative substitutions. A conservative substitution for an amino acid in an immunogenic peptide as described herein may be selected from other members of the class to which the amino acid belongs. For example, it is well-known in the art of protein biochemistry that an amino acid belonging to a grouping of amino acids having a particular size or characteristic (such as charge, hydrophobicity, and hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH$_2$. Likewise, biologically active analogs of a polypeptide containing deletions or additions of one or more contiguous or noncontiguous amino acids that do not eliminate a functional activity of the peptide are also contemplated.

In one or more embodiments, an CSP-targeting peptide as described herein can include a peptide with at least 60%, at least 66%, at least 73%, at least 80%, at least 86%, or at least 93% sequence similarity to amino acids SEQ ID NO:2. That is, an CSP-targeting polypeptide can include a total of no more than six, no more than five, no more than four, no more than three, no more than two, or no more than one amino acid deletions and non-conservative amino acid substitutions compared to SEQ ID NO:2.

In one or more embodiments, a CSP-targeting peptide as described herein can include a peptide with at least 60%, at least 66%, at least 73%, at least 80%, at least 86%, or at least 93% sequence identity to SEQ ID NO:2. That is, a CSP-targeting polypeptide can include a total of no more than six, no more than five, no more than four, no more than three, no more than two, or no more than one amino acid deletions and amino acid substitutions compared to SEQ ID NO:2.

In one or more embodiments, a CSP-targeting peptide as described herein can be designed to provide additional sequences, such as, for example, the addition of added C-terminal or N-terminal amino acids that can, for example, facilitate purification by trapping on columns or use of antibodies. Such tags include, for example, histidine-rich tags that allow purification of polypeptides on nickel columns. Such gene modification techniques and suitable additional sequences are well known in the molecular biology arts.

The virus-like particle (VLP) can include any particle that includes viral protein assembled to structurally resemble the virus from which they are derived, but lack enough of the viral genome so that they are non-replicative and, therefore, noninfectious. A VLP may, therefore, include at least some of the viral genome, but the viral genome is genetically modified so that the viral genes responsible for infectivity and replication are inactivated. Exemplary VLPs include, but are not limited to, VLPs of Qβ, MS2, PP7, AP205, or other bacteriophage coat proteins, the capsid and core proteins of Hepatitis B virus, measles virus, Sindbis virus, rotavirus, foot-and-mouth-disease virus, Norwalk virus, the retroviral GAG protein, the retrotransposon Ty protein pl, the surface protein of Hepatitis B virus, human papilloma virus, human polyoma virus, RNA phages, Ty, frphage, GA-phage, AP 205-phage and, in particular, Qβ-phage, Cowpea chlorotic mottle virus, cowpea mosaic virus, human papilloma viruses (HPV), bovine papilloma viruses, porcine parvovirus, parvoviruses such as B19, porcine (PPV) and canine (CPV) parvovirues, caliciviruses (e.g. Norwalk virus, rabbit hemorrhagic disease virus [RHDV]), animal hepadnavirus core Antigen VLPs, filamentous/rod-shaped plant viruses, including but not limited to Tobacco Mosaic Virus (TMV), Potato Virus X (PVX), *Papaya* Mosaic Virus (PapMV), Alfalfa Mosaic Virus (AIMV), and Johnson Grass Mosaic Virus (JGMV), insect viruses such as flock house virus (FHV) and tetraviruses, polyomaviruses such as Murine Polyomavirus (MPyV), Murine Pneumotropic Virus (MPtV), BK virus (BKV), and JC virus (JCV).

The antigenic CSP peptides may be coupled to immunogenic carriers via chemical conjugation or by expression of genetically engineered fusion partners. The coupling does not necessarily need to be direct, but can occur through linker sequences. More generally, in the case that antigenic peptides either fused, conjugated, or otherwise attached to an immunogenic carrier, spacer sequence, or linker sequence are typically added at one or both ends of the antigenic peptides. Such linker sequences generally comprise sequences recognized by the proteasome, proteases of the endosomes or other vesicular compartment of the cell.

In one embodiment, the antigenic CSP peptide may be displayed as fusion protein with a subunit of the immunogenic carrier. Fusion of the peptide can be effected by inserting the CSP antigenic peptide amino acid sequence into the immunogenic carrier primary sequence, or by fusion to either the N-terminus or C-terminus of the immunogenic carrier.

When the immunogenic carrier is a VLP, the chimeric antigenic peptide-VLP subunit can be capable of self-assembly into a VLP. VLP displaying epitopes fused to their subunits are also herein referred to as chimeric VLPs. For example, European Application No. EP90310204A (European Patent No. EP0421635 B1) describes the use of chimeric hepadnavirus core antigen particles to present foreign peptide sequences in a virus-like particle.

Flanking amino acid residues may be added to either end of the sequence of the antigenic peptide to be fused to either end of the sequence of the subunit of a VLP, or for internal insertion of such peptide sequence into the sequence of the subunit of a VLP. Glycine and serine residues are particularly favored amino acids to be used in the flanking sequences added to the peptide to be fused. Glycine residues confer additional flexibility, which may diminish the potentially destabilizing effect of fusing a foreign sequence into the sequence of a VLP subunit.

In one or more embodiments, the immunogenic carrier is a VLP of a RNA phage, preferably Qβ. The major coat proteins of RNA phages spontaneously assemble into VLPs upon expression in bacteria such as, for example, *E. coli*. Fusion protein constructs wherein antigenic peptides have been fused to the C-terminus of a truncated form of the A1 protein of Qβ, or inserted within the A1 protein have been described (Kozlovska et al., 1996, *Intervirology* 39: 9-15). Assembly of Qβ particles displaying the fused epitopes typically involves the presence of both the A1 protein-antigen fusion and the wild type coat protein to form a mosaic particle. However, embodiments involving VLPs, and in particular the VLPs of the RNA phage Qβ coat protein, that are exclusively composed of VLP subunits having an antigenic peptide fused thereto, are contemplated.

The production of mosaic particles may be effected in a number of ways. In one exemplary approach, efficient display of the fused epitope on the VLPs is mediated by the expression of the plasmid encoding the Qβ A1 protein fusion having a UGA stop codon between the coat protein and the coat protein extension in an *E. coli* strain harboring a plasmid encoding a cloned UGA suppressor tRNA, which leads to translation of the UGA codon into Trp (pISM3001 plasmid). In a second exemplary approach, the coat protein gene stop codon is modified into UAA, and a second plasmid expressing the A1 protein-antigen fusion is co-transformed. The second plasmid encodes a different antibiotic resistance and the origin of replication is compatible with the first plasmid. In a third exemplary approach, Qβ coat protein and the A1 protein-antigen fusion are encoded in a bicistronic manner, operatively linked to a promoter such as the Trp promoter.

Further VLPs suitable for fusion of antigens or antigenic determinants are described in, for example, International Patent Application No. PCT/IB2002/004132 (International Publication No. WO 03/024481 A2) and include bacteriophage fr, RNA phage MS-2, capsid protein of papillomavirus, retrotransposon Ty, yeast and also Retrovirus-like-particles, HIV2 Gag, Cowpea Mosaic Virus, parvovirus VP2 VLP, HBsAg (U.S. Pat. No. 4,722,840). Examples of chimeric VLPs suitable for use as the immunogenic carrier include those described in Kozlovska et al., 1996, *Intervirology* 39:9-15. Further examples of VLPs suitable for use as the immunogenic carrier include, but are not limited to, HPV-1, HPV-6, HPV-11, HPV-16, HPV-18, HPV-33, HPV-45, CRPV, COPV, HIV GAG, Tobacco Mosaic Virus, Virus-like particles of SV-40, Polyomavirus, Adenovirus, Herpes Simplex Virus, Rotavirus, and Norwalk virus.

In a preferred embodiment, a vaccine construct containing the CSP peptide containing SEQ ID NO:1 is synthesized by conjugating the peptide to Qβ bacteriophage VLPs using a bifunctional cross-linker (SMPH). The CSP peptide can be modified to include a linker peptide to the C-terminus (e.g., a GGGC linker sequence; SEQ ID NO:3) or the N-terminus (e.g., a CGGG linker sequence; SEQ ID NO:4). The SMPH cross-linker conjugates free amines on the surface of the Qβ VLPs to the cysteine residue of the linker peptide. In this synthesis methodology, the Qβ VLP is purified from free, unconjugated crosslinker, and then reacted with the CSP peptide at a molar ratio of about 10 peptides:1 VLP For any recombinantly expressed antigenic CSP peptide described herein (whether or not coupled to an immunogenic carrier), this disclosure describes the nucleic acid that encodes the peptide or protein, as is an expression vector comprising the nucleic acid, and a host cell containing the expression vector (autonomously or chromosomally inserted). This disclosure further describes a method of recombinantly producing the peptide or protein by expressing it in a host cell with or without further isolating the immunogen.

Thus, this disclosure describes an isolated nucleic acid sequence that encodes any embodiment of an antigenic CSP peptide described herein. In one or more embodiments, the isolated nucleic acid encodes an immunogenic portion of SEQ ID NO:1 such as, for example, the amino acid sequence of SEQ ID NO:2. Given the amino acid sequence of any immunogenic CSP peptide, a person of ordinary skill in the art can determine the full scope of polynucleotides that encode that amino acid sequence using conventional, routine methods.

As used herein, the term "nucleic acid" or "oligonucleotide" refers to polynucleotides such as deoxyribonucleic acid (DNA) or ribonucleic acid (RNA). Nucleic acids include but are not limited to genomic DNA, cDNA, mRNA, iRNA, miRNA, tRNA, ncRNA, rRNA, and recombinantly produced and chemically synthesized molecules such as aptamers, plasmids, anti-sense DNA strands, shRNA, ribozymes, nucleic acids conjugates, and oligonucleotides. A nucleic acid may be single-stranded, double-stranded, linear, or covalently circularly closed molecule. A nucleic acid can be isolated. The term "isolated nucleic acid" means that the nucleic acid (i) was amplified in vitro, for example via polymerase chain reaction (PCR), (ii) was produced recombinantly by cloning, (iii) was purified, for example, by cleavage and separation by gel electrophoresis, (iv) was synthesized, for example, by chemical synthesis, or (vi) extracted from a sample. A nucleic acid might be introduced—i.e., transfected—into cells. When RNA is used to transfect cells, the RNA may be modified by stabilizing modifications, capping, or polyadenylation.

As used herein "amplified DNA" or "PCR product" refers to an amplified fragment of DNA of defined size. Various techniques are available and well known in the art to detect PCR products. PCR product detection methods include, but are not restricted to, gel electrophoresis using agarose or polyacrylamide gel and adding ethidium bromide staining (a DNA intercalant), labeled probes (radioactive or non-radioactive labels, southern blotting), labeled deoxyribonucleotides (for the direct incorporation of radioactive or non-radioactive labels) or silver staining for the direct visualization of the amplified PCR products; restriction endonuclease digestion, which relies on agarose gel electrophoresis, polyacrylamide gel electrophoresis, or high-performance liquid chromatography (HPLC); dot blots, using the hybridization of the amplified DNA on specific labeled probes (radioactive or non-radioactive labels); high-pressure liquid chromatography using ultraviolet detection; electro-chemiluminescence coupled with voltage-initiated chemical reaction/photon detection; and direct sequencing using radioactive or fluorescently labeled deoxyribonucleotides for the determination of the precise order of nucleotides with a DNA fragment of interest, oligo ligation assay (OLA), PCR, qPCR, DNA sequencing, fluorescence, gel electrophoresis, magnetic beads, allele specific primer extension (ASPE) and/or direct hybridization.

Generally, nucleic acid can be extracted, isolated, amplified, or analyzed by a variety of techniques such as those described by Green and Sambrook, Molecular Cloning: A Laboratory Manual (Fourth Edition), Cold Spring Harbor Laboratory Press, Woodbury, NY 2,028 pages (2012); or as described in U.S. Pat. Nos. 7,957,913; 7,776,616; 5,234,809; and 9,012,208. Examples of nucleic acid analysis include, but are not limited to, sequencing and DNA-protein interaction. Sequencing may be by any method known in the art. DNA sequencing techniques include classic dideoxy sequencing reactions (Sanger method) using labeled terminators or primers and gel separation in slab or capillary, and next generation sequencing methods such as sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Separated molecules may be sequenced by sequential or single extension reactions using polymerases or ligases as well as by single or sequential differential hybridizations with libraries of probes.

This disclosure also describes a host cell including any of the isolated nucleic acid sequences and/or proteins described herein. Thus, this disclosure encompasses translation of a nucleic acid (e.g., an mRNA) by a host cell to produce an immunogenic CSP peptide and/or a VLP that displays an immunogenic CSP peptide.

The nucleic acid constructs of the present invention may be introduced into a host cell to be altered, thus allowing expression of the CSP peptide and/or CSP VLP within the cell, thereby generating a genetically engineered cell. A variety of methods are known in the art and suitable for introducing a nucleic acid into a cell, including viral and non-viral mediated techniques. Examples of typical non-viral mediated techniques include, but are not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion. Other methods of transfection include proprietary transfection reagents such as LIPOFECTAMINE (Thermo Fisher Scientific, Inc., Waltham, MA), HILYMAX (Dojindo Molecular Technologies, Inc., Rockville, MD), FUGENE (Promega Corp., Madison, WI), JETPEI (Polyplus Transfection, Illkirch, France), EFFECTENE (Qiagen, Hilden, Germany) and DreamFect (OZ Biosciences, Inc USA, San Diego, CA).

The nucleic acid constructs described herein may be introduced into a host cell to be altered, thus allowing expression within the cell of the protein encoded by the nucleic acid. A variety of host cells are known in the art and suitable for protein expression. Examples of typical cell used for transfection and protein expression include, but are not limited to, a bacterial cell, a eukaryotic cell, a yeast cell, an insect cell, or a plant cell such as, for example, *E. coli, Bacillus, Streptomyces, Pichia pastoris, Salmonella typhimurium, Drosophila* S2, *Spodoptera* SJ9, CHO, COS (e.g., COS-7),3T3-F442A, HeLa, HUVEC, HUAEC, NIH 3T3, Jurkat, 293, 293H, or 293F.

In one or more embodiments, the antigenic CSP peptide can be chemically coupled to the immunogenic carrier using techniques well known in the art. Conjugation can occur to allow free movement of peptides via single point conjugation (e.g., either N-terminal or C-terminal point) or as a locked down structure where both ends of peptides are conjugated to either an immunogenic carrier protein or to a scaffold structure such as a VLP. Conjugation occurs via conjugation chemistry known to those skilled in the art such as via cysteine residues, lysine residues, or another carboxy moiety. Thus, for example, for direct covalent coupling, it is possible to use a carbodiimide, glutaraldehyde, or N-[y-maleimidobutyryloxy] succinimide ester, using common commercially available hetero-bifunctional linkers such as 1-cyano dimethylaminopyridinium tetrafluoroborate (CDAP) or succinimidyl 3-(2-pyridyldithio)propionate (SPDP).

Examples of conjugation of peptides, particularly cyclized peptides, to a protein carrier via acylhydrazine peptide derivatives are described in, for example, International Patent Application No. PCT/EP2003/004551 (International Publication No. WO 2003/092714 A1). After the coupling reaction, the immunogen can easily be isolated and purified using, for example, a dialysis method, a high performance liquid chromatography method, a gel filtration method, a fractionation method, etc. Peptides terminating with a cysteine residue (preferably with a linker outside the cyclized region) may be conveniently conjugated to a carrier protein via maleimide chemistry.

When the immunogenic carrier is a VLP, several antigenic peptides, either having an identical amino acid sequence or a different amino acid sequence, may be coupled to a single VLP particle, leading preferably to a repetitive and ordered structure presenting several antigenic determinants in an oriented manner as described in International Patent Applications PCT/IB1999/001925 (International Publication No. WO 00/032227), PCT/IB2002/004132 (International Publication No. WO 2003/024481), PCT/IB2002/000166 (International Publication No. WO 02/056905), and PCT/EP2003/007572 (International Publication No. WO 2004/007538). Thus, the antigenic peptide displayed by one VLP subunit in a VLP may the same or different than the antigenic peptide displayed by a second VLP subunit in the same VLP. In other embodiments, one or several antigen molecules can be attached to one VLP subunit. A specific feature of the VLP of the coat protein of RNA phages, and in particular of the Qβ coat protein VLP, is thus the possibility to couple several antigens per subunit. This allows for the generation of a dense antigen array.

Another feature of VLPs derived from RNA phage is their high expression yield in bacteria that allows production of large quantities of material at affordable cost. Moreover, the use of the VLPs as carriers allows the formation of robust antigen arrays and conjugates, respectively, with variable antigen density. In particular, the use of VLPs of RNA phages, and in particular the use of the VLP of RNA phage Qβ coat protein, allows a very high antigen density to be achieved.

Compositions and Methods of Treatment

The CSP-targeting VLP may be used to treat a subject having, or at risk of having, a condition characterized, at least in part, by cells that express CSP. Such conditions include, but are not limited to, malaria.

As used herein, "treat" or variations thereof refer to reducing, limiting progression, ameliorating, or resolving, to any extent, the symptoms or signs related to a condition. A "sign" or "clinical sign" refers to an objective physical finding relating to a particular condition capable of being found by one other than the patient. A "symptom" refers to any subjective evidence of disease or of a patient's condition.

A "treatment" may be therapeutic or prophylactic. "Therapeutic" and variations thereof refer to a treatment that ameliorates one or more existing symptoms or clinical signs associated with a condition. "Prophylactic" and variations thereof refer to a treatment that limits, to any extent, the development and/or appearance of a symptom or clinical sign of a condition. Generally, a "therapeutic" treatment is initiated after the condition manifests in a subject, while "prophylactic" treatment is initiated before a condition manifests in a subject. Typically, the CSP-targeted VLP will be used prophylactically to reduce the likelihood that the malaria parasite reaches the liver.

Treatment that is prophylactic—e.g., initiated before a subject manifests a symptom or clinical sign of the condition such as, for example, while a tumor remains subclinical—is referred to herein as treatment of a subject that is "at risk" of having the condition. As used herein, the term "at risk" refers to a subject that may or may not actually possess the described risk. Thus, for example, a subject "at risk" of developing a condition is a subject possessing one or more risk factors associated with the condition such as, for example, genetic predisposition, ancestry, age, sex, geographical location, lifestyle, or medical history. Thus, the CSP-targeted VLP may be administered before a subject manifests a symptom or clinical sign of malaria. In one or more embodiments, the CSP-targeted VLP may be administered before a subject travels to a geographical location where malaria may be prevalent.

Accordingly, a composition can be administered before, during, or after the subject first exhibits a symptom or clinical sign of the condition (e.g., malaria). Treatment initiated before the subject first exhibits a symptom or clinical sign associated with the condition may result in decreasing the likelihood that the subject experiences clinical evidence of the condition compared to a subject to which the composition is not administered, decreasing the severity of symptoms and/or clinical signs of the condition, and/or completely resolving the condition. Treatment initiated after the subject first exhibits a symptom or clinical sign associated with the condition may result in decreasing the severity of symptoms and/or clinical signs of the condition compared to a subject to which the composition is not administered, and/or completely resolving the condition.

Thus, the method includes administering an effective amount of the composition to a subject having, or at risk of having, a condition characterized, at least in part, by cells that express CSP. In this aspect, an "effective amount" is an amount effective to reduce, limit progression, ameliorate, or resolve, to any extent, a symptom or clinical sign related to the condition.

Thus, the CSP-targeting Qβ VLP described herein may be formulated with a pharmaceutically acceptable carrier. As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with the CSP-targeting Qβ VLP without causing any undesirable biological effects or interacting in a deleterious manner with any of the other components of the pharmaceutical composition in which it is contained.

The CSP-targeting Qβ VLP may therefore be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical composition can be administered to a mucosal surface, such as by administration to, for example, the nasal or respiratory mucosa (e.g., by spray or aerosol). A composition also can be administered via a sustained or delayed release.

Thus, an CSP-targeting Qβ VLP may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant (whether an ADVAX adjuvant or other adjuvant), a skin penetration enhancer, a colorant, a fragrance, a flavoring, a moisturizer, a thickener, and the like.

A formulation may be conveniently presented in unit dosage form and may be prepared by methods well known in the art of pharmacy. Methods of preparing a composition with a pharmaceutically acceptable carrier include the step of bringing the CSP-targeting Qβ VLP into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

The amount of CSP-targeting Qβ VLP administered can vary depending on various factors including, but not limited to, the cancer being treated, the weight, physical condition, and/or age of the subject, and/or the route of administration. Thus, the absolute weight of CSP-targeting Qβ VLP included in a given unit dosage form can vary widely, and depends upon factors such as the species, age, weight, and physical condition of the subject, and/or the method of administration. Accordingly, it is not practical to set forth generally the amount that constitutes an amount of CSP-targeting Qβ VLP effective for all possible applications. Those of ordinary skill in the art, however, can readily determine the appropriate amount with due consideration of such factors.

In one or more embodiments, the method can include administering sufficient CSP-targeting Qβ VLP to provide a dose of, for example, from about 50 ng/kg to about 1 mg/kg to the subject, although in one or more embodiments the methods may be performed by administering CSP-targeting Qβ VLP in a dose outside this range.

In one or more embodiments, the method includes administering sufficient CSP-targeting Qβ VLP to provide a minimum dose of at least 50 ng/kg such as, for example, at least 100 ng/kg, at least 200 ng/kg, at least 300 ng/kg, at least 400 ng/kg, at least 500 ng/kg, at least 600 ng/kg, at least 700 ng/kg, at least 800 ng/kg, at least 900 ng/kg, at least 1 µg/kg, at least 2 µg/kg, at least 5 µg/kg, at least 10 µg/kg, at least 20 µg/kg, at least 50 µg/kg, at least 100 µg/kg, at least 200 µg/kg, or at least 500 µg/kg.

In one or more embodiments, the method includes administering sufficient CSP-targeting Qβ VLP to provide a maximum dose of no more than 1 mg/kg, no more than 500 µg/kg, no more than 250 µg/kg, no more than 200 µg/kg, no more than 150 µg/kg, no more than 100 µg/kg, no more than 50 µg/kg, no more than 25 µg/kg, no more than 10 µg/kg, no more than 5 µg/kg, no more than 2 µg/kg, no more than 1 µg/kg, no more than 800 ng/kg, no more than 600 ng/kg, no more than 500 ng/kg, no more than 400 ng/kg, no more than 300 ng/kg, no more than 250 ng/kg, no more than 150 ng/kg, no more than 100 ng/kg, no more than 50 ng/kg, or no more than 25 ng/kg.

In one or more embodiments, the method includes administering sufficient CSP-targeting Qβ VLP to provide that falls within a range having as endpoints any minimum dose listed above and any maximum dose listed above that is greater than the minimum does. For example, in one or more embodiments, the method can includes administering sufficient CSP-targeting Qβ VLP to provide a dose of from 200 ng/kg to about 10 μg/kg to the subject, for example, a dose of from about 700 ng/kg to about 5 μg/kg.

In one or more embodiments, CSP-targeting Qβ VLP may be administered, for example, from a single dose to multiple doses per week, although in one or more embodiments the method can be performed by administering CSP-targeting Qβ VLP at a frequency outside this range. When multiple doses are used within a certain period, the amount of each dose may be the same or different. For example, a dose of 1 mg per day may be administered as a single dose of 1 mg, two 0.5 mg doses, or as a first dose of 0.75 mg followed by a second dose of 0.25 mg. Also, when multiple doses are used within a certain period, the interval between doses may be the same or be different.

In certain embodiments, CSP-targeting Qβ VLP may be administered at minimum frequency of at least once per year such as, for example, at least once every six months, at least once every four months, at least once every three months, at least once every two months, at least once per month, or at least once every two weeks.

In certain embodiments, CSP-targeting Qβ VLP may be administered at maximum frequency of no more than once per week such as, for example, no more than once every two weeks, no more than once per month, no more than once every two months, no more than once every three months, no more than once every six months, or once per year.

In one or more embodiments, CSP-targeting Qβ VLP may be administered at a frequency defined by a range having as endpoints any minimum frequency listed above and any maximum frequency listed above that is more frequent than the minimum frequency.

The duration of administration of an antigenic CSP peptide described herein, e.g., the period of time over which an antigenic CSP peptide is administered, can vary, depending on any of a variety of factors, e.g., patient response, etc. For example, an antigenic CSP peptide can be administered over a period of time ranging from about one day to about one week, from about two weeks to about four weeks, from about one month to about two months, from about two months to about four months, from about four months to about six months, from about six months to about eight months, from about eight months to about one year, from about one year to about two years, or from about two years to about four years, or more. In one or more embodiments, the CSP-targeting Qβ VLP may be administered as a once off treatment. In other embodiments, the CSP-targeting Qβ VLP may be administered for the life of the subject. In certain embodiments, the CSP-targeting Qβ VLP may be administered may be administered monthly (or every four weeks) until effective.

In one or more embodiments, the CSP-targeting Qβ VLP may be administered at an initial frequency for an initial period and then administered at a lower frequency thereafter. For example, a dosing regimen may include administering three doses of the CSP-targeting Qβ VLP at a frequency of once per month (i.e., an initial dose followed by a second dose one month after the initial dose) followed by an additional dose six months after the initial dose.

When an CSP-targeting Qβ VLP composition is used for prophylactic treatment, it may be generally administered for priming and/or boosting doses. Boosting doses, when administered, are adequately spaced (e.g., yearly) to boost the level of circulating antibody that has fallen below a desired level. Boosting doses may include an CSP-targeting peptide either with or in the absence of the original immunogenic carrier. A booster composition may include an alternative immunogenic carrier or may be in the absence of any carrier. Moreover, a booster composition may be formulated either with or without adjuvant.

In some cases, the method can further include administering to the subject an additional therapeutic agent effective for treating the condition (e.g., malaria). For example, therapy involving the CSP-targeting Qβ VLP may be combined with conventional therapies for malaria.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure (s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The present invention is illustrated by the following examples. It is to be understood that the particular examples, materials, amounts, and procedures are to be interpreted broadly in accordance with the scope and spirit of the invention as set forth herein.

EXAMPLES

Production and Characterization of VLP-Based Vaccines

CIS43 VLPs were produced as described in (Jelinková et al., 2022, npj Vaccines 6, 13). L9 VLPs were produced similarly; the fifteen amino acid L9 epitope peptide (SEQ ID NO: 2) was synthesized (GenScript Biotech Corp., Piscataway, NJ) and modified to contain a C-terminal GGGC (SEQ ID NO:3) linker sequence (NANPNVDPNANPNVDGGGC; SEQ ID NO:5) and was conjugated directly to surface lysines on Qβ bacteriophage VLPs using the bidirectional crosslinker succinimidyl 6-[(beta-maleimidopropionamido) hexanoate] (SMPH; Thermo Fisher Scientific Inc., Waltham, MA) as previously described (Tumban et al. PLOS ONE 6, e23310 (2011)). The efficiency of conjugation was assessed by gel electrophoresis using a 10% SDS denaturing polyacrylamide gel followed by analysis using IMAGEJ software to calculate the average peptide density per VLP. Presence of the L9 peptide on L9 VLPs was confirmed by ELISA. Briefly, 250 ng of VLPs were used to coat wells of an ELISA plate. Wells were probed with dilutions of mAb L9, followed by a 1:4000 dilution of horseradish peroxidase (HRP) labeled goat anti-human IgG (Jackson ImmunoResearch Laboratories, Inc., West Grove, PA). The reaction was developed using 3,3',5, 5'-tetramethylbenzidine (TMB) substrate (Thermo Fisher Scientific Inc., Waltham, MA) and stopped using 1% HCl. Reactivity was determined by measuring optical density at 450 nm ($OD_{450}$) using an ACCUSKAN plate reader (Fisher Scientific, Waltham, MA).

Mouse Immunization Studies

For the initial evaluation of immunogenicity, groups of 4-5-week-old female Balb/c mice (Jackson ImmunoResearch Laboratories, Inc., West Grove, PA) were immunized intramuscularly with 5 μg of L9 VLPs without exogenous adjuvant. Mice were boosted twice after the initial prime, weeks 4 and 7 post-prime. For challenge studies, 7-8-week-old C57Bl/6 mice (n=6-7/group) were immunized with 5 μg doses of L9 VLPs, CIS43 VLPs, or wild-type control Qβ VLPs in combination with 20 μL of ADVAX-3 adjuvant (5 mg/mL). Mice were immunized at days 0, 28, and 56. An additional group of naïve (unimmunized) mice were included in this experiment.

Quantitating Antibody Responses

Serum antibodies against full-length CSP were detected by ELISA using recombinant CSP expressed in *Pseudomonas fluorescens* (Noe et al. PLoS One 9, e107764 (2014)) (Leidos, Inc., Reston, VA) as the coating antigen, as described previously (Jelinkova et al. NPJ Vaccines 6, 13 (2021)). Anti-CSP antibody concentrations were determined by generating a standard curve using known concentrations of the anti-CSP mouse mAb 2A10. Competition ELISAs were performed by using the CSP ELISA protocol with the following modifications: after mouse serum was added to the plate, 40 ng of the human mAb L9 (at a final concentration of 400 ng/mL) was added to each well and incubated for 30 minutes. L9 mAb binding to CSP was detected using HRP-labeled goat anti-human IgG at a 1:4000 dilution.

Mouse Pb-PfCSP-Luc Sporozoite Mosquito Challenge

Mice were challenged directly by using infected mosquitos four weeks following their third final vaccination. *Anopheles stephensi* mosquitos were infected by blood feeding on Pb-PfCSP-Luc infected mice. Prior to challenge, mice were anesthetized with 2% Avertin, and then exposed to six mosquitos for a blood meal for 10 minutes. Following feeding, the number of mosquitos positive for a blood meal was determined. Liver luminescence was assessed 42 hours post challenge by intraperitoneally injecting anesthetized mice with 100 μl D-luciferin (30 mg/ml) and then determining liver luminescence using an IVIS Spectrum Imaging System (Perkin Elmer, Waltham, MA). Beginning four days after challenge, blood smears were collected daily and then evaluated by Giemsa staining for parasitemia.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure (s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

```
Sequence Listing Free Text
                                           SEQ ID NO: 1
EDNEKLRKPK HKKLKQPADG NPDPNANPNV DPNANPNVDP

NANPNVDPNA NPNANPNANP NANPNA

SEQ ID NO: 2
NANPNVDPNA NPNVD

SEQ ID NO: 3
GGGC

SEQ ID NO: 4
CGGG

SEQ ID NO: 5
NANPNVDPNA NPNVDGGGC
```

What is claimed is:

1. An immunogen comprising:
   an immunogenic carrier comprising a Qβ bacteriophage virus-like particle (VLP); and
   an antigenic malaria circumsporozoite protein (CSP) junction region peptide comprising NANPNVDPNANPNVD (SEQ ID NO:2) linked to the immunogenic carrier.

2. The immunogen of claim 1, wherein the immunogenic carrier is linked to the CSP peptide through a succinimidyl-6-[β-maleimidopropionamido]hexanoate (SMPH) cross-linker molecule.

3. The immunogen of claim 1, further comprising a second antigenic malaria circumsporozoite protein (CSP) peptide.

4. The immunogen of claim 3, wherein SEQ ID NO:2 and the second antigenic CSP peptide are displayed on a single VLP.

5. The immunogen of claim 3, wherein the second antigenic CSP peptide comprises amino acids 21-35 of SEQ ID NO:1.

6. A composition comprising the immunogen of claim 1.

7. The composition of claim 6, comprising:
   a first population of VLPs displaying SEQ ID NO:2; and
   a second population of VLPs displaying a second antigenic CSP peptide.

8. The composition of claim 6, further comprising an adjuvant.

9. The composition of claim 8, wherein the adjuvant comprises a CpG oligonucleotide.

10. A method of treating malaria in an individual, the method comprising administering a therapeutically effective amount of the composition of claim 1 to the individual.

11. The method of claim 10, wherein the method further comprises administering to the individual at least one additional therapeutic agent for treating malaria.

12. The method of claim 10, wherein the immunogen further comprises a second antigenic malaria circumsporozoite protein (CSP) peptide.

13. The method of claim 12, wherein SEQ ID NO:2 and the second antigenic CSP peptide are linked to a single carrier.

14. The method of claim 12, wherein the composition comprises:
   a first population of immunogens comprising the immunogen of claim 1; and
   a second population of immunogens comprising:
      a second population of immunogenic carriers; and
      the second CSP peptide linked to the second population of immunogenic carriers.

15. The method of claim 12, wherein the second antigenic CSP peptide comprises amino acids 21-35 of SEQ ID NO:1.

16. The method of claim 10, wherein the composition is administered to the individual before the individual manifests a symptom or clinical sign of malaria.

17. The method of claim 14, wherein the second population of immunogenic carriers comprises a Qβ virus-like particle (VLP).

18. A vaccine comprising the composition of claim 6.

19. A method of treating malaria in an individual, the method comprising administering to the individual a therapeutically effective amount of the vaccine of claim 18.

20. The method of claim 19, wherein the method further comprises administering to the individual at least one additional therapeutic agent for treating malaria.

21. The method of claim 19, wherein the vaccine further comprises a second antigenic malaria circumsporozoite protein (CSP) peptide.

22. The method of claim 21, wherein SEQ ID NO:2 and the second antigenic CSP peptide are linked to a single carrier.

23. The method of claim 21, wherein the vaccine comprises:
   a first population of immunogens comprising the immunogen of claim 1; and
   a second population of immunogens comprising:
      a second population of immunogenic carriers; and
      the second CSP peptide linked to the second population of immunogenic carriers.

24. The method of claim 21, wherein the second antigenic CSP peptide comprises amino acids 21-35 of SEQ ID NO:1.

25. The method of claim 19, wherein the vaccine is administered to the individual before the individual manifests a symptom or clinical sign of malaria.

26. A method of treating Plasmodium falciparum blood stage parasitemia in an individual, the method comprising administering to the individual a therapeutically effective amount of the vaccine of claim 18.

27. The method of claim 26, wherein the method further comprises administering to the individual at least one additional therapeutic agent for treating malaria.

28. The method of claim 26, wherein the vaccine further comprises a second antigenic malaria circumsporozoite protein (CSP) peptide.

29. The method of claim 28, wherein SEQ ID NO:2 and the second antigenic CSP peptide are linked to a single carrier.

30. The method of claim 28, wherein the vaccine comprises:
   a first population of immunogens comprising the immunogen of claim 1; and
   a second population of immunogens comprising:
      a second population of immunogenic carriers; and
      the second CSP peptide linked to the second population of immunogenic carriers.

31. The method of claim 28, wherein the second antigenic CSP peptide comprises amino acids 21-35 of SEQ ID NO:1.

32. The method of claim 26, wherein the vaccine is administered to the individual before the individual manifests a symptom or clinical sign of Plasmodium falciparum blood stage parasitemia.

\* \* \* \* \*

SEQUENCE LISTING

```
Sequence total quantity: 5
SEQ ID NO: 1            moltype = AA  length = 66
FEATURE                 Location/Qualifiers
source                  1..66
                        mol_type = protein
                        organism = Homo sapiens
SEQUENCE: 1
EDNEKLRKPK HKKLKQPADG NPDPNANPNV DPNANPNVDP NANPNVDPNA NPNANPNANP    60
NANPNA                                                              66

SEQ ID NO: 2            moltype = AA  length = 15
FEATURE                 Location/Qualifiers
source                  1..15
                        mol_type = protein
                        organism = Homo sapiens
SEQUENCE: 2
NANPNVDPNA NPNVD                                                    15

SEQ ID NO: 3            moltype = AA  length = 4
FEATURE                 Location/Qualifiers
source                  1..4
                        mol_type = protein
                        organism = synthetic construct
SEQUENCE: 3
GGGC                                                                 4

SEQ ID NO: 4            moltype = AA  length = 4
FEATURE                 Location/Qualifiers
source                  1..4
                        mol_type = protein
                        organism = synthetic construct
SEQUENCE: 4
CGGG                                                                 4

SEQ ID NO: 5            moltype = AA  length = 19
FEATURE                 Location/Qualifiers
source                  1..19
                        mol_type = protein
                        organism = synthetic construct
SEQUENCE: 5
NANPNVDPNA NPNVDGGGC                                                19
```